United States Patent [19]

Schultz

[11] Patent Number: 4,559,160
[45] Date of Patent: Dec. 17, 1985

[54] HIGHLY STABLE DICHLOROBENZIDINE DIHYDROCHLORIDE SLURRY AND A METHOD FOR PREPARING SUCH

[75] Inventor: Steven C. Schultz, North Muskegon, Mich.

[73] Assignee: Bofors Nobel, Inc., Muskegon, Mich.

[21] Appl. No.: 578,550

[22] Filed: Feb. 9, 1984

[51] Int. Cl.$^4$ .......................... C09K 3/00; B01J 13/00; C09D 11/00
[52] U.S. Cl. .................................. 252/182; 252/311; 106/308 N
[58] Field of Search ........................... 252/182, 1, 311; 106/21, 23, 308 N

[56] References Cited
U.S. PATENT DOCUMENTS
4,341,701 7/1982 Pechey et al. ..................... 106/23 X FOREIGN PATENT DOCUMENTS
2112797 5/1983 United Kingdom .

Primary Examiner—Teddy S. Gron
Assistant Examiner—Virginia B. Caress
Attorney, Agent, or Firm—Price, Heneveld, Huizenga & Cooper

[57] ABSTRACT

A dichlorobenzidine dihydrochloride (DCB) slurry is produced by adding DCB to a dilute mineral acid carrier composed of hydrochloric acid, sulfuric acid or phosphoric acid, by maintaining the DCB concentration within the range such that the diamine amount constitutes from about 35% to about 50% by weight, and by blending the slurry with a high shear device in order to break up any clumps of DCB and to reduce the size of the individual particles of DCB. The resulting slurry is very fluid, yet has an extremely low solids settling rate.

21 Claims, No Drawings

HIGHLY STABLE DICHLOROBENZIDINE DIHYDROCHLORIDE SLURRY AND A METHOD FOR PREPARING SUCH

BACKGROUND OF THE INVENTION

This invention relates to a dichlorobenzidine dihydrochloride slurry having both a low solid settling rate and a low viscosity. The invention also relates to a method for preparing such a slurry.

The chemical compound 3,3-dichlorobenzidine dihydrochloride, hereinafter referred to as DCB, is the primary ingredient used in the production of yellow pigments. The pigments so produced are used extensively in the printing industry as the predominant source of coloring for yellow ink.

DCB is produced as either a wet or a dry powder. It is then packaged in drums and shipped to the pigment manufacturer. To begin the pigment manufacturing process, the DCB is poured into large mixing tanks and then reacted with various other chemicals to yield a yellow compound.

Both the wet powdered and the dry powdered forms of DCB are very dusty. A substantial amount of DCB dust is generated throughout the packaging, shipping and pigment manufacturing processes.

In 1974, the Occupational Safety and Health Agency (OSHA) designated DCB as a "cancer suspect agent". Because of this designation, the handling and usage of DCB is strictly regulated (see 29 CFR 1910.1007).

The regulations promulgated by OSHA are designed to minimize human and environmental exposure to the DCB powder and dust. For example, 29 CFR 1910.1007 requires DCB to be handled in isolated structures which are fully enclosed and impervious to the passage of DCB. The isolated structure must be provided with a ventilation system which constantly pumps fresh air into the system and withdraws contaminated air from the system. The exhaust air, before it can be discharged back into the environment, must be scrubbed in order to remove any suspended DCB dust.

The regulations also require the drums containing the DCB to be unloaded under drum dusting hoods. The DCB contaminated air that is sucked up by the hoods must then be scrubbed before being discharged into the environment. Further, the drums must be decontaminated and disposed of after use. The solution used to rinse out the drums must also be decontaminated.

The regulations further require the employees who handle DCB powder to wear full protective clothing, including gloves, impervious body suits and air-supplied dust hoods, in order to minimize their exposure to DCB powder and/or dust. Working in such protective clothing is very cumbersome. Employees are also required to shower and change their clothes after working in an isolated structure where DCB is handled or used.

The handling of powdered DCB is an expensive and labor intensive process. In order to comply with OSHA regulations, substantial amounts of money must be spent to construct the isolated system, to purchase the ventilation and pollution control equipment, and to operate such facilities on a day-to-day basis.

Many of the problems associated with the handling of powdered DCB could be eliminated or reduced by making DCB available in a non-dusty form. The present invention provides a non-dusty DCB composition in the form of a DCB slurry.

A serious problem associated with liquid slurries is that such compositions have high solids settling rates. Slurries having high solids settling rates must be constantly stirred in order to keep the particles in suspension. If the slurry is not stirred, the particles that settle out will clog drains, pipes, filters and pumps.

Another serious problem associated with liquid slurries is that such compositions, in order to be economical, must have a high solids concentration. However, a slurry having a high solids concentration is usually quite thick and viscous. Thick, high viscosity slurries do not flow easily and thus are difficult to pump.

These problems associated with settling rates and viscosity are inter-related. One can attain a slurry having a low solid settling rate by increasing the slurry viscosity. However, such a slurry, while stable, is extremely difficult and expensive to pump. On the other hand, one can attain a fluid, low viscosity slurry by decreasing the concentration of the suspended solids or by adding thinning agents. However, such a slurry, while easy to pump, generally has a high settling rate.

SUMMARY OF THE INVENTION

The present invention provides a liquid DCB slurry having both a low solids settling rate and a low viscosity. In the slurry of the present invention, the DCB particles remain in nearly complete suspension for at least seventy-two hours. This low solids settling rate has been achieved by adding certain mineral acids to the slurry and by maintaining the DCB concentration within a narrow range, i.e., by means other than substantially increasing the slurry viscosity. Since the slurry viscosity is relatively low, the slurry of the present invention is very fluid and can thus be efficiently pumped and resuspended.

These desirable properties for a liquid-based slurry, i.e., an extremely low solids settling rate in conjunction with the low viscosity, have been achieved by adding certain mineral acids such as hydrochloric acid, sulfuric acid and/or phosphoric acid to the liquid carrier (namely, water, as is disclosed in detail and claimed hereinafter), by maintaining the DCB concentration within a certain narrow range, and by reducing the size of the suspended DCB particles. It was discovered that the DCB concentration of the slurry and the DCB particle size dramatically affect the solids settling rate. It was also discovered that the presence of certain mineral acids in the liquid carrier chemically stabilizes that DCB so that the solids can be suspended as a homogenous slurry. It was further discovered that, in the presence of a mineral acid and a specific DCB concentration, the ultimate slurry viscosity needed to achieve a stable slurry is lower than that viscosity which would be needed if the DCB concentration was outside of the claimed range. The combination of these discoveries has led to the formulation of a DCB slurry which has both a low solid settling rate and a low viscosity.

The liquid DCB slurry of the present invention eliminates or reduces many of the problems associated with the handling of powdered DCB. The DCB slurry can be transported and stored in large enclosed tanks, thus, eliminating the need to package the DCB in drums. Consequently, the need to decontaminate and dispose of used drums is also eliminated. Further, the handling of a DCB slurry does not generate any DCB dust. The use of a non-dust generating DCB composition reduces the potential for human and environmental exposure to the cancer suspect agent, eliminates the need for employees to wear full impervious body suits and air-supplied hoods while unloading DCB slurry, eliminates the need to unload the DCB under dust hoods, and substantially reduces the volume of air which must be circulated and decontaminated.

The liquid DCB slurry of the present invention, because of its low viscosity and low solids settling rate, eliminates or reduces many of the problems associated with the handling of a liquid slurry. The need to constantly resuspend the slurry during storage is eliminated because the slurry has such a low solids settling rate. Since the slurry settles so slowly, the problems associated with settled particles clogging pipes, valves and pumps is substantially reduced. Moreover, the slurry, because of its low viscosity, is very fluid; it thus flows easily and can be efficiently pumped. This eliminates the need to purchase and use costly and powerful pumps.

These and other objects, advantages and features of the DCB composition of the present invention and the method for producing the same will be more fully understood and appreciated by reference to the detailed description and the appended claims.

DESCRIPTION OF THE PREFERRED EMBODIMENT

The present invention basically relates to liquid (aqueous) DCB slurry having both a low solids settling rate and a low viscosity. Powdered DCB is admixed with a liquid carrier which contains a small amount of a specified mineral acid, such as hydrochloric acid, sulfuric acid and/or phosphoric acid. The acid tends to stabilize the DCB so that a low viscosity, homogenous slurry can be formed. Further, the DCB concentration of the final slurry is carefully controlled. Slurries which are fluid yet have low solids settling rates are attained when the DCB concentration is kept within the range such that the diamine concentration is from between 35% to 50% by weight. As noted hereinafter (EXAMPLE III), the concentration of what is referred to herein as "DCB" (the chemical compound 3, 3-dichlorobenzidine dihydrochloride), is as it is analyzed by diamine concentration. No reliable technique is believed available in the industry for accurately analyzing the complete compound dichlorobenzidine dihydrochloride. Conventional analysis is made by analyzing the compound as a diamine, i.e. without the two hydrochloride groups. The percentages of DCB referred to herein are as analyzed by diamine concentration. The solids settling rate, absent grinding or blending, increases dramatically when the DCB concentration is less than about 35% by weight. At DCB concentrations above 50% by weight the solids settling rate is low but the slurry is extremely thick, and would be very difficult to pump. Finally, the slurry is ground in a wet grinder or blended with a high shear device in order to break up clumps of DCB particles and to reduce the size of the individual DCB particles. Reducing the size of the DCB particles increases the slurry viscosity. The increase in viscosity and the reduction in particle size substantially reduces the solid settling rate of the slurry. Because of the stabilizing effects of the particular mineral acid and the controlled DCB concentration, the viscosity needed to attain a low solids settling rate need not be raised above 50 Poise in accordance with the preferred embodiments of this invention. A slurry having a viscosity of 50 P or less can be very easily pumped.

The combination of adding the mineral acid to the liquid carrier, maintaining the DCB within a narrow range, and increasing the slurry viscosity by blending or grinding results in a slurry having both an acceptably low viscosity and a low solids settling rate. The solids settling rate is measured by determining the settling volume ratio. To obtain the settling volume ratio, a sample of slurry is poured into a graduated cylinder and the volume of the slurry is recorded. This volume is known as the "total slurry volume". The sample is then allowed to settle for a given period of time, for example, for one hour. After the settling period has elapsed, the volume of the slurry which is still in suspension is measured. This volume is known as the "settled slurry volume". The settling volume ratio can then be determined:

$$\text{Settling volume ratio} = \frac{\text{settled slurry volume}}{\text{total slurry volume}}$$

A slurry in which the particles are in complete suspension has a slurry volume ratio of 1.0. For a given period of settling, say for one hour, the higher the settling volume ratio the lower the solids settling rate.

A slurry has an acceptably low solids settling rate if, for a given period of time, the settling volume ratio is approximately 0.94 or above. Slurries having a settling volume ratio of less than 0.94 for a given period of time must either be constantly or intermittently stirred in order to keep the particles in suspension and to avoid the problems associated with sedimentation.

With regards to a DCB slurry, it may take up to three days to transport a load of such slurry from the DCB manufacturer to the pigment manufacturer. Further, the pigment manufacturer may have to store the slurry in a tank for several days before using it. Thus, in order to avoid the need to constantly agitate the DCB slurry, the slurry should have a settling volume ratio of approximately 0.94 or above after seventy-two hours.

It was originally thought that a DCB slurry which could easily be pumped, yet which had a low solids settling rate could be attained by suspending the DCB in water and by keeping the DCB concentration rather low. It was discovered, however, that an aqueous based slurry having a low DCB concentration was very fluid but had an unacceptably high solids settling rate. Example I illustrates the high solids settling rate of a 20% DCB by weight slurry:

EXAMPLE I

The Settling Volume Ratio of an Aqueous Based DCB Slurry

The purpose of this test was to determine whether an aqeuous based DCB slurry having a low DCB concentration had an acceptably high solids settling rate. For this test, a 20% DCB by weight slurry was prepared and allowed to settle. The settling volume ratio was obtained as described above after 5, 10 and 20 minutes. The results are set forth in Table I:

TABLE I

THE SETTLING VOLUME RATIO OF A 20% DCB BY WEIGHT, WATER-BASED SLURRY

| Sample | SETTLING VOLUME RATIO | | |
|---|---|---|---|
| | Initial Value | After 5 Min. | After 20 Min. |
| 20% DCB | 1.00 | .85 | .53 |

TABLE I-continued

THE SETTLING VOLUME RATIO OF A
20% DCB BY WEIGHT, WATER-BASED SLURRY

| Sample | SETTLING VOLUME RATIO | | |
|---|---|---|---|
| | Initial Value | After 5 Min. | After 20 Min. |
| in Water | | | |

After only 20 minutes, the 20% DCB slurry had a settling volume ratio of 0.53; that is, within 20 minutes, the DCB particles had settled out of approximately 50% of the total slurry volume. A slurry having such an extremely high solids settling rate would have to be constantly stirred during transport or storage in order to keep the DCB particles in suspension.

It was thought that a DCB slurry which could easily be pumped and which had low solids settling rate could be attained merely by increasing the DCB concentration. It was discovered that the solids settling rate indeed decreased as the DCB concentration was increased. However, the slurry became much thicker and more viscous as the DCB concentration was increased. Example II illustrates how the solids settling rate decreases and the slurry viscosity increases as the DCB concentration is increased.

EXAMPLE II

The Effect of Increasing the DCB Concentration on the Solids Settling Rate

The purpose of this test was to determine what effect increasing the DCB concentration of the aqueous based slurry had on the solids settling rate. For this test a 40% by weight DCB slurry was prepared and allowed to settle. The settling volume ratios were obtained as described after 24 hours and after 72 hours. Viscosity was measured using a Brookfield Viscometer, Spindle LV-2, 12 rpm. The results are set forth below:

TABLE II

THE SETTLING VOLUME RATIOS OF A 40% DCB BY WEIGHT, WATER-BASED SLURRY

| Sample | Viscosity (in poise) | SETTLING VOLUME RATIO | |
|---|---|---|---|
| | | After 24 Hours | After 72 Hours |
| 40% DCB in Water | 110 | .959 | .886 |

Increasing the DCB concentration from 20% by weight to 40% by weight dramatically increased the settling volume ratio. However, the viscosity of such a slurry was extremely high. The thick, viscous slurry formed by suspending high levels of DCB in water would be extremely difficult to pump, and, if it had to be pumped, would necessitate the use of powerful expensive pumps. From the results of Examples I and II, it was concluded that a pumpable slurry having a low solids settling rate could not be obtained merely by suspending DCB in water.

One aspect of the present invention was the discovery that the presence of the mineral acid in the liquid carrier decreased the slurry viscosity without substantially affecting the solids settling rate. The mineral acids which had such effects on the slurry viscosity and slurry solids settling rates are hydrochloric acid, sulfuric acid, and phosphoric acid. The preferred mineral acid is hydrochloric acid. Not all mineral acids were effective. For example, nitric acid was ineffective.

The free mineral acid concentration of the slurry of the present invention ranges from about 1% to about 10% by weight. Preferably, the free mineral acid ranges from about 1% to about 5% by weight. The "free" mineral acid concentration is the percentage by weight of the acid added to the liquid carrier to the weight of the completed slurry. The term is not intended to include acids which may be present as impurities in the added DCB.

The following examples illustrate how the presence of certain mineral acids in the liquid carrier decreases the slurry viscosity without substantially affecting the slurry solids settling rate.

EXAMPLE III

The Effect of Mineral Acids on the Viscosity and Settling Volume Ratio of Various DCB Slurries The purpose of this test was to determine what effect the addition of various amounts of certain mineral acids to the aqueous carrier had on the settling volume ratio and the consistency of various DCB slurries. For this test, several different DCB/mineral acid slurries were prepared. For example, two liters of a 40% DCB/1% HCl by weight slurry was prepared by diluting 71 grams of 31% HCl in 886 grams of water and then admixing 1,243 grams of 70.8% DCB (as analyzed by diamine) to the dilute mineral acid carrier. Other DCB/mineral acid slurries were prepared in a similar manner. A sample of each slurry was then poured into a graduated cylinder and allowed to settle. The settling volume ratios were determined for each sample after one hour and after 24 hours. Viscosity was measured on a Brookfield Viscometer, Spindle LV-2, 12 rpm. The results of this test are set forth below:

TABLE III

EFFECT OF VARIOUS MINERAL ACIDS ON SLURRY VISCOSITY AND STABILITY

| Sample | Viscosity (in Poise) | Settling Volume Ratio (after 24 hours) |
|---|---|---|
| 40% DCB, 0% Mineral Acid | 110 | .959 |
| 35% DCB, 1% HCl | | .833 |
| 35% DCB, 3% HCl | 1.5 | .794 |
| 35% DCB, 5% HCl | 4.2 | .881 |
| 35% DCB, 10% HCl | | .458 |
| 40% DCB, 1% HCl | 6.3 | .942 |
| 40% DCB, 3% HCl | 9.7 | .941 |
| 40% DCB, 5% HCl | | .940 |
| 40% DCB, 10% HCl | | .940 |
| 45% DCB, 1% HCl | | .915 |
| 45% DCB, 3% HCl | 13.0 | .947 |
| 45% DCB, 5% HCl | 20.0 | .930 |
| 45% DCB, 10% HCl | | .912 |
| 40% DCB, 3% $H_2SO_4$ | 2.8 | .838 |
| 40% DCB, 3% $H_3PO_4$ | 37.0 | .99 |
| 40% DCB, 3% $HNO_3$ | Did not form a slurry | |

Looking at the 40% DCB/3% mineral acid slurries, it can be seen that when the mineral acid is HCl, the viscosity is very low and the 24 hour settling volume ratio is above 0.94. With $H_3PO_4$, the settling volume ratio is above 0.94, but the viscosity is much higher. With $H_2SO_4$, the viscosity is very low, but the 24 hour settling volume ratio is less than 0.94. From these results, it was concluded that HCl was the preferred mineral acid.

With the various DCB/HCl slurries it can be seen that, for a given DCB concentration, the highest settling volume ratio was attained when the HCl concentration ranged from 1% to about 5% by weight. With the 35% DCB/HCl and 45% DCB/HCl slurries the settling volume ratios generally descrease as the HCl concentration approaches 10% by weight. As to the 40% DCB/HCl solutions, the settling volume ratios remain fairly constant at all HCl concentrations tested. From these results it was concluded that the mineral acid concentration should range from about 1% to about 10% by weight, preferably from about 1% to about 5% by weight. These results also suggested that the DCB concentration might have a stabilizing effect on the slurry.

From these results, it was concluded that the addition of certain mineral acids to the liquid carrier was an important factor in formulating a low viscosity slurry having a low solids settling rate.

A second aspect of the present invention was the discovery that the DCB concentration of a dilute mineral acid based slurry had a substantial effect in the solid settling rate. It is generally accepted that the solids settling rate of a slurry can be decreased by increasing the solids concentration to rather high levels, i.e., to levels above 50% by weight. Such slurries however are very thick and extremely difficult to pump. Surprisingly, however, it was discovered that the lowest solids settling rates were obtained when the DCB concentration was less than 50% by weight. Not only were the settling rates fairly low, but the slurries themselves were quite fluid.

The effect of varying the DCB concentration on the settling volume ratio is illustrated in the examples set forth below:

EXAMPLE IV

Effect of DCB Concentration on the Settling Volume Ratio of a Slurry

The purpose of this test was to determine what effect the DCB concentration had on the solids settling rate of a slurry. Several slurries having various DCB concentrations and HCl concentrations were prepared. A sample of each slurry was poured into a graduated cylinder and allowed to settle. The settling volume ratio for each sample was then measured after one hour and/or after 24 hours. The results of this test are set forth in Table IV:

TABLE IV
EFFECT OF DCB CONCENTRATION ON THE SETTLING VOLUME RATIO

| DCB Concentration | HCl Concentration | SETTLING VOLUME RATIO | |
|---|---|---|---|
| | | After 1 Hour | After 24 Hours |
| 30% | 1% | .663 | |
| 30% | 5% | .780 | |
| 35% | 3% | .841 | .794 |
| 36% | 3% | | .930 |
| 38% | 3% | | .949 |
| 40% | 3% | .994 | .974 |
| 42% | 3% | | .965 |
| 43% | 3% | | .962 |
| 45% | 3% | .982 | .947 |
| 47% | 3% | | .944 |
| 50% | 3% | | .962 |

The settling volume ratio increases steadily as the DCB concentration is increased from 30% to about 40% by weight. The largest increase is seen when the concentration is increased from 35% to 36%. Unexpectedly, however, the settling volume ratio begins to decrease as the DCB concentration is increased from 40% to 47% by weight. The highest settling volume ratio is achieved when the DCB concentration is approximately 40% by weight. These examples clearly illustrate the importance of DCB concentration on the settling volume ratio.

The DCB concentration also affects the consistency and thus the pumpability of the slurry. At DCB concentrations above 45% the slurry begins to get fairly thick. About 50% by weight, the slurry becomes extremely thick, having a consistency on the order of that of wet cement, i.e., viscosity in excess of 500 Poise.

By adding the mineral acid to the aqueous carrier and by maintaining the DCB concentration within the 38% to 50% by weight range, a slurry having both a low solids settling rate (a settling volume ratio of 0.94 or above after 24 hours) and a low viscosity (viscosity less than 20.0 Poise), can be attained. This slurry can be transported or stored for up to 24 hours without having to be resuspended and can be pumped easily and efficiently.

It was found that a slurry having a settling volume ratio of at least 0.94 after 72 hours could be attained by increasing the viscosity of the DCB/mineral acid slurry. The viscosity can be increased by reducing the size of the DCB particles. This can be done either by grinding the slurry with a wet grinder or by blending it with a high shear device.

In another aspect of this invention, it was discovered that the final slurry viscosity needed to attain a settling volume ratio of at least 0.94 after 72 hours is related to the DCB concentration. The lowest viscosities needed to attain such a settling volume ratio occur when the DCB concentration ranges from about 36% to about 44%. When the DCB is less than 36% or greater than 44%, the viscosity needed to attain a comparable settling volume ratio is higher. When the DCB concentration is below 30% by weight the viscosity must be substantially increased in order to attain the necessary settling rate. In addition, a slurry having such a low DCB concentration would not be economical to ship. When the DCB concentration is above 50% by weight, the slurry is too thick to be economically pumped.

In the product and process of the present invention, the slurry is blended or ground for an amount of time sufficient to yield a slurry having a viscosity within the range from about 10 Poise to about 500 Poise. Preferably, the viscosity is within the range from about 10 Poise to about 50 Poise.

Examples VI and VII illustrate how reducing the size of the DCB clumps and particles increases the slurry viscosity while decreasing the solids settling rate. Example VIII illustrates how the ultimate viscosity of the slurry that is needed to attain a settling volume ratio of 0.94 is related to the DCB concentration.

EXAMPLE VI

The Effect of Blending the Slurry with a High Shear Device

The purpose of this test was to determine what effect blending the DCB slurry had on the settling volume ratio. For this test, a 40% DCB/1% HCl slurry was prepared and divided into five samples; one of which was not blended and four of which were blended for different lengths of time. Each sample was poured into a graduated cylinder and allowed to settle. The settling volume ratio for each sample was then determined after one hour, 13 hours and 336 hours of settling. Particle size was determined by observing a small sample of each slurry under a microscope. Viscosity was measured using a Brookfield Viscometer Spindle LV-2, 6-12 rpm. The results of this test are set forth in Table VI:

TABLE VI
EFFECT OF BLENDING ON THE VISCOSITY
AND STABILITY OF A 40% DCB/3% HCl SLURRY

| Blending Time (Minutes) | Particle Size | Viscosity (Poise) | SETTLING VOLUME RATIO | | |
|---|---|---|---|---|---|
| | | | 1 Hr. | 13 Hrs. | 336 Hrs. |
| 0 | ~200 μ (Many clumps) | 6.3 | .882 | .787 | .775 |
| 1 | ~100 μ | 5.1 | .926 | .878 | .851 |
| 3 | | 9.0 | .958 | .959 | .892 |
| 5 | | 13.2 | .984 | .985 | .957 |
| 10 | ~20 μ (very few clumps) | 15.5 | .983 | .989 | |

Example VI illustrates how blending reduces the size of the suspended DCB particles and increases the slurry viscosity. The combined effect of reducing the particle size and increasing the slurry viscosity is to increase the settling volume ratio of that slurry to an acceptably high level.

EXAMPLE VII

The Effect of Grinding the Slurry with a Wet Grinder

The purpose of this test was to determine what effect grinding the slurry had on particle size and the settling volume ratio. For this test, a 40% DCB/3% HCl slurry was prepared and divided into five samples. One sample served as the control. Four samples were ground with a SWECO wet grinder for 5, 10, 20 or 40 minutes. The viscosity of each sample was determined using a Brookfield Viscometer, Spindle LV-2, 6-30 rpm. The samples were then allowed to settle for 72 hours after which time the settling volume ratios were measured as previously described. The results are set forth in Table VII:

TABLE VII
EFFECT OF GRINDING ON THE VISCOSITY
AND STABILITY OF A 40% DCB/3% HCl SLURRY

| Minutes ground | Particle Size | Viscosity (Poise) | SETTLING VOLUME RATIO (After 72 hours) |
|---|---|---|---|
| 0 | 50-100 μ | 2.3 | .810 |
| 5 | 10 μ | 15.0 | .921 |
| 10 | 10 μ | 28.0 | .939 |
| 20 | 5 μ | 60.0 | .970 |
| 40 | Most less than ~5 μ | 1200 | .995 |

Example VII illustrates how grinding the slurry decreases the particle size and increases slurry viscosity. The effect of this is to increase the settling volume ratio. The 40% DCB/3% HCl slurry must have a viscosity of more than 28 Poise in order to have a settling volume ratio of 0.94 or above after 72 hours. By increasing the viscosity above 100 Poise, an extremely high settling volume ratio can be achieved; however, such a slurry is very thick and thus very difficult to pump.

EXAMPLE VIII

Effect of the DCB Concentration on the Viscosity Needed to Obtain an Acceptably High Settling Volume Ratio The purpose of this test was to determine what effect the DCB concentration had on the actual viscosity needed to attain a settling volume ratio of 0.94 or above after at least 72 hours. For this test, various DCB/HCl slurries were prepared. Each sample was blended for a given period of time and then allowed to settle for at least 72 hours. The settling volume ratios were then determined as previously described. The results are set forth in Table VIII:

TABLE VIII
EFFECT OF DCB CONCENTRATION ON SLURRY VISCOSITY

| DCB | HCl | Initial Viscosity | Blended Time | Blended Viscosity | SETTLING VOLUME RATIO After at least 72 Hours |
|---|---|---|---|---|---|
| 40 | 1 | 6.25 | 0 | 6.25 | .775 |
| 40 | 1 | 6.25 | 1 | 5.3 | .851 |
| 40 | 1 | 6.25 | 3 | 9.0 | .892 |
| 40 | 1 | 6.25 | 5 | 13.2 | .957 |
| 40 | 1 | 6.25 | 10 | 15.5 | .965 |
| 35 | 3 | 1.5 | 10 | 8.0 | .966 |
| 35 | 5 | 4.2 | 10 | 16.0 | .971 |
| 45 | 3 | 13.0 | 10 | 36.0 | .971 |
| 45 | 5 | 20.0 | 10 | 45.0 | .978 |

This example clearly illustrates that the actual viscosity needed to attain the settling volume ratio of 0.94 after 72 hours is related to the DCB concentration. With a 40% DCB/1% HCl slurry, i.e., at the optimal DCB concentration, a viscosity of only 13.2 Poise is needed to attain a settling volume ratio of at least 0.94 after more than 72 hours. In order to attain a comparable settling volume ratio after 72 hours, a 35% DCB/5% HCl slurry must have a viscosity of 16.0 Poise and a 45% DCB/5% HCl slurry must have a viscosity of 45.0 Poise. This example clearly shows the interaction between the DCB concentration and slurry viscosity.

Notice also how even the 35% DCB slurries, when blended, have settling volume ratios above 0.94 after 72 hours. Combining these results with the results of examples IV and V, it was concluded that maintaining the DCB concentration within the range from about 35% to about 50% by weight was an important factor in formulating a slurry which could be easily pumped and which had a low settling rate. Therefore, the DCB concentration of the present invention ranges from about 35% to about 50% by weight, preferably from about 38% to about 43%, optimally at about 40% by weight.

In Example IX, the preferred method for preparing the slurry of the present invention is illustrated.

EXAMPLE IX

In this example, a 400 pound production batch of 40% DCB by weight/3% HCl by weight slurry was prepared in accordance with the present invention. First, 38.7 pounds of 31% HCl was diluted with 137.3 pounds (or 16.5 gallons) of water to yield a 7% HCl by weight solution. Next, 224 pounds of wet powdered DCB (71.4% amine) was added to the dilute acid carrier and thoroughly mixed. In the third step, the homogenous slurry was ground by a wet grinder for approximately 35.0 minutes. The final DCB slurry had a viscosity of 20 Poise and a settling volume ratio of 0.945 after approximately 108 hours.

It is believed that the importance of adding a mineral acid to the carrier and of maintaining the DCB concentration within a range of from about 35% to about 50% by weight, for the purpose of attaining a low viscosity, high settling volume ratio slurry, is illustrated by the above test results. It will also be appreciated that various substitutions and modifications can be made without departing from the spirit and broader aspects of the invention, as set forth more particularly in the appended claims.

The embodiments of the invention in which an exclusive property or privilege is claimed are defined as follows:

1. A stable dichlorobenzidine dihydrochloride slurry, consisting essentially of:
   (a) dichlorobenzidine dihydrochloride in an amount such that the diamine amount constitutes from about 35% to about 50% by weight;
   (b) free mineral acid, selected from the group consisting of hydrochloric acid, phosphoric acid and sulfuric acid, in an amount ranging from about 1% to about 10% by weight;
   (c) water in an amount ranging from about 40% to about 50% by weight; and
   (d) having a viscosity within the range of about 10 Poise to about 500 Poise.

2. The slurry of claim 1 wherein the viscosity is within the range of about 10 Poise to about 50 Poise.

3. The slurry of claim 1 wherein the free mineral acid concentration ranges from about 1% to about 5% by weight.

4. The slurry of claim 1 wherein the dichlorobenzidine dihydrochloride concentration ranges from about 38% to about 43% by weight.

5. The slurry of claim 2 wherein the free mineral acid concentration ranges from about 1% to about 5% by weight.

6. The slurry of claim 3 wherein the dichlorobenzidine dihydrochloride concentration ranges from about 38% to about 43% by weight.

7. The slurry of claim 4 wherein the viscosity is within the range of about 10 Poise to about 50 Poise.

8. The slurry of claim 5 wherein the dichlorobenzidine dihydrochloride concentration ranges from about 38% to about 43% by weight.

9. The slurry of claim 1 wherein the mineral acid is sulfuric acid.

10. The slurry of claim 1 wherein the mineral acid is phosphoric acid.

11. The slurry of claim 1, 3, 5, 7 or 8 wherein the mineral acid is hydrochloric acid.

12. A stable dichlorobenzidine dihydrochloride slurry, consisting essentially of:
   (a) dichlorobenzidine dihydrochloride in an amount such that the diamine amount constitutes approximately 40% by weight;
   (b) free mineral acid, selected from the group consisting of hydrochloric acid, phosphoric acid, and sulfuric acid, in an amount ranging from about 1% to about 5% by weight;
   (c) water in an amount ranging from about 40% to about 50% by weight; and
   (d) a viscosity within the range from about 10 Poise to about 50 Poise.

13. The slurry of claim 12 wherein the mineral acid is hydrochloric acid.

14. A method for preparing a liquid dichlorobenzidine dihydrochloride slurry having a low solids settling rate, which comprises the steps of:
   (a) providing a dilute aqueous mineral acid solution, chosen from the group consisting of hydrochloric acid, phosphoric acid or sulfuric acid;
   (b) admixing dichlorobenzidine dihydrochloride with the dilute mineral acid solution to yield a homogeneous slurry having a dichlorobenzidine dihydrochloride concentration such that the diamine concentration is from about 35% to about 50% by weight;
   (c) controlling the free mineral acid concentration to be within the range of 1% to 10%; and
   (d) causing the slurry viscosity to be a value within the range from about 10 Poise to about 500 Poise.

15. The method as recited in claim 14 wherein the slurry viscosity is caused to be a value within the range from about 10 Poise to about 50 Poise.

16. The method as recited in claim 15 wherein the dichlorobenzidine dihydrochloride concentration ranges from about 38% to about 43% by weight.

17. The method as recited in claim 16 wherein the mineral acid of the dilute mineral acid solution is hydrochloric acid.

18. The method as recited in claim 17 wherein the mineral acid of the dilute mineral acid solution is phosphoric acid.

19. The method as recited in claim 16 wherein the mineral acid of the dilute mineral acid solution is sulfuric acid.

20. The method as recited in claim 17 wherein the viscosity is caused to be a value within the range from about 10 Poise to about 50 Poise by grinding the slurry with a wet grinder.

21. The method as recited in claim 17 wherein the viscosity is caused to be a value within the range from about 10 Poise to about 50 Poise by blending the slurry with a high shear device.

* * * * *